United States Patent [19]

Haas

[11] Patent Number: 4,566,798

[45] Date of Patent: Jan. 28, 1986

[54] METHOD FOR CALIBRATING A REFLECTOMETER CONTAINING BLACK AND WHITE REFERENCES DISPLACED FROM THE SAMPLE POSITION

[75] Inventor: Daniel D. Haas, Rochester, N.Y.

[73] Assignee: Eastman Kodak Company, Rochester, N.Y.

[21] Appl. No.: 550,692

[22] Filed: Nov. 10, 1983

[51] Int. Cl.[4] .......................... G01N 21/55; G01J 1/02
[52] U.S. Cl. ..................................... 356/448; 356/243
[58] Field of Search ............... 356/443, 448, 445, 236, 356/243, 446; 250/228; 364/526

[56] References Cited

U.S. PATENT DOCUMENTS

| 3,832,070 | 8/1974 | Cox | 356/445 |
| 3,874,799 | 4/1975 | Isaacs et al. | 250/228 X |
| 4,029,419 | 6/1977 | Schumann et al. | |

FOREIGN PATENT DOCUMENTS 0088601  9/1983  European Pat. Off. .

OTHER PUBLICATIONS

Hunter, Richard S., "A Multipurpose Photoelectric Reflectometer", National of Standards, J.O.S.A., vol. 30, Nov. 1940, pp. 536-559.

Par. 1-3 and 3-3 of the Owner's Manual for the "Reflection Densitometer Model RD-400 Quanta Log" manufactured by Macbeth Instrument Corp., Newburgh, N.Y., dated 1968.

*Primary Examiner*—Vincent P. McGraw
*Assistant Examiner*—Robert Thompson
*Attorney, Agent, or Firm*—Dana M. Schmidt

[57] ABSTRACT

A method is disclosed for calibrating a reflectometer using black and white references observed in locations optically different from the sample location. Dark and light standards are selected to have reflectance values, while examined in the detection location of the test elements, that are within ±0.005 and ±0.05 of the values of the black and white references, respectively, when examined in a location displaced from the detection location of the test elements. Such standards are then read on a referee reflectometer having "ideal" black and white references, and the reflectances so read on the referee reflectometer are recorded for use as calibrating factors in making reflectance readings for the test elements.

3 Claims, 5 Drawing Figures

METHOD FOR CALIBRATING A REFLECTOMETER CONTAINING BLACK AND WHITE REFERENCES DISPLACED FROM THE SAMPLE POSITION

FIELD OF THE INVENTION

This invention relates to a method for calibrating a reflectometer, and more particularly to corrections needed because of displacement of the reflectometer references from the location of the samples or test elements read by the reflectometer.

BACKGROUND OF THE INVENTION

In commonly owned copending, allowed application U.S. Ser. No. 354,859, now U.S. Pat. No. 4,424,191, filed on Mar. 4, 1982, by Raymond F. Jakubowicz, entitled "Analyzer Featuring Loading and Unloading Means for a Storage Chamber, and Common Drive Means", corresponding to European Patent Publication No. 88,601 published on Sept. 14, 1983, there is described a simplified analyzer for use in small offices, such as doctor's offices. Incubated test elements are pushed through a photometer station, one at a time, by a pusher blade that has a black reference and a white reference coated on the underside of the pusher blade. Because the purpose of the analyzer is to provide an inexpensive way to measure the analytes body liquids using test elements containing all the necessary reagents preincorporated therein, such reference coatings are inexpensively made. That is, the black reference may not be an ideal black (perfectly absorptive), and the white reference may not be an ideal white (perfectly reflective). In such a case, it is possible for a test element to produce a reflection density that is darker than the "black" reference, or lighter than the "white" reference.

The most conventional calculation of reflection density $D_R$ follows the equation $$D_R = -\log_{10}[(A/D_{sample} - A/D_{black\ ref})/(A/D_{white\ ref} - A/D_{black\ ref})] \quad (1)$$

where A/D represents the analog-to-digital electrical signal generated by the reflectance of either the sample (usually the test element), black reference, or white reference. It will be readily apparent that the possible case noted above of a blacker or a whiter test element (than the reference) will throw off the calibration curve, at best. At worst, in the case of a blacker test element, it produces a negative reflectance, an artificial concept. It can be shown that, to correct for such non-ideality in the black and white references equation (1) should be modified as follows:

$$D_R^{ideal} = -\log_{10}(R_{sample}^{corrected}), \text{ or } D_R^{ideal} =$$
$$-\log_{10}[R_{sample}^{uncorr} \times (R_{white}^{effective} - R_{black}^{effective}) + R_{black}^{effective}] \quad (1a)$$

wherein $R_{sample}^{uncorr}$ is exactly the argument of the log of equation (1), that is:

$$R_{sample}^{uncorr} = (A/D_{sample} - A/D_{black\ ref})/(A/D_{white\ ref} - A/D_{black\ ref}); \quad (2)$$

and $R_{white}^{effective}$ and $R_{black}^{effective}$ are the *effective* reflectances of the white reference coating and of the black reference coating, respectively. Thus, $R^{uncorr}$ is adjusted (equation 1a)) to become the corrected reflectance by, first, multiplying it with $(R_{white}^{effective} - R_{black}^{effective})$, and then adding to the product term $R_{black}^{effective}$.

Such effective reflectances are determined using a referee photometer or reflectometer wherein the black and white primary references are carefully (and thus, more costly) selected to be blacker and whiter, respectively, than the blackest and whitest sample that is likely to be read thereon. In other words, the referee reflectometer is selected to have substantially ideal black and white primary references. A representative example of such an instrument is the reflectometer obtained from Zeiss Company under the trademark "Zeiss DMC-26".

The conventional method of calibration by ascertaining the values of $R_{white}^{effective}$ and $R_{black}^{effective}$ as the corrective factors for equation (1a) above, has been to remove the non-ideal black and white references from the inexpensive analyzer, and read them as intrinsic reflectances on the referee reflectometer. This, however, ignores an important factor about the location of such black and white reference coatings. As described in the aforesaid application, the black and white reference coatings are located in the test reflectometer at a position that is optically different from the detection position of the detectable portion of the test element carrying the liquid sample. That is, the reference coatings are positioned for detection displaced from the detection position of the test elements, thus producing a variation in the length of the optical path. Although the displacement of such two positions can be made to be as small as possible, there is still about 0.5 mm difference between the two. Such displacement can be essentially eliminated by requiring the operator to send through the black and white references as test elements every time a sample is being read. However, this alternative has several disadvantages. One is that repeating a "run" of the black and white reference as a special kind of test element along with every sample test element runs the risk of the reference "test elements" being lost since they would not be permanent parts of the analyzer. Another is that positioning the black and white references at the detection location of the test elements prevents the apparent reflectance of such references from being altered or corrected by changing the displacement distance. Instead, the intrinsic reflectance has to be modified by a chemical or structural change to the coating itself. Finally, the analyzer of the aforesaid application requires the photometer to contact the test elements conveyed through it. If the black and white references were also read by contact, a transparent protective, and expensive, coating would have to be added to prevent scratching.

Notwithstanding the advantage of such a displacement, displacement has been objectionable because the apparent reflectance of the black or white reference is altered from what it would have been if the references were located the same distance from the light source as were the test elements, as is well known. Such alterations in apparent reflectance can produce an error in detected reflection density which is as much as 50%-70% in the conventional method.

SUMMARY OF THE INVENTION

I have discovered a method by which the above error in apparent reflectance can be corrected, as a calibration procedure, so that the advantages of having a displacement in the detection location of the black and white references can be retained.

More specifically, there is provided a method of calibrating a reflectometer of the type used to determine reflection densities of a test element, the reflectometer containing a black reference and a white reference that are detected in a first location that is optically different from the location of such test elements when positioned for detection. The method features the use of calibrating factors representing the effective reflectance for each of the black and white references, which compensate for the optically different locations of the black and white references compared to that of the test elements. The steps of the method comprise: (a) selecting a dark standard and a light standard which, when measured on the first (test) reflectometer in the test element detection location, produce the same amount of uncorrected reflectance, within ±0.005 and ±0.05, respectively, as do the black and white references when measured on the reflectometer while in the first location; (b) measuring the respective reflectances of the dark and light standards on a second referee reflectometer having ideal black and white references; and (c) recording the measured reflectances obtained in step (b) as the effective reflectances for the black and white references.

In one embodiment of this invention, the dark and light standards noted above are selected so that they produce, when measured on the first photometer, an uncorrected reflectance that is within ±0.005 and ±0.05 of, respectively, zero and 1.0.

Thus, the invention advantageously features a method of calibrating a reflectometer having black and white references located for detection in a position different from the detection location of the test elements, without creating an error in the apparent reflectance of the references that translates into an error in the determination of concentration of analyte in the test elements.

A related advantageous feature is that this invention enables the test reflectometer to determine corrected sample reflectances as accurately as does the referee reflectometer.

It is another related advantageous feature of the invention that such black and white references can be made permanent parts of the instrument, thus avoiding the risk of being lost.

It is a further related advantageous feature of this invention that the apparent reflectance of such black or white reference can be altered merely by changing the detection location, again without introducing an error in the determination of concentration of the test elements.

Another advantageous feature of the invention is that such method permits the use of a contact reflectometer without requiring that such black and white references be given a protective coating.

Still another advantageous feature is that it allows the use of non-ideal references.

Other advantageous features will become apparent upon reference to the following Description of the Preferred Embodiments, when read in light of the attached drawings.

DESCRIPTION OF THE PREFERRED EMBODIMENTS

The subject invention is described in connection with a preferred analyzer and reflectometer, wherein the latter is a contact reflectometer, and test elements containing a liquid analyte. In addition, it is applicable to any analyzer or reflectometer wherein the black and white references are positioned in a detection location that is displaced and optically different from that of the detection location of the test elements, whether or not either or both of the references are non-ideal. Herein, the term "displaced references" refers to the displacement of the detection location of the references from the detection location of the test element. The method of this invention is also useful for measuring the reflectance or reflection density of test elements which do not receive liquids, such as dyed cloth, paper, photographic coatings, and plastics.

A variety of test elements is useful within the invention. Preferably the test elements are constructed to receive a liquid containing analytes and to produce a change detectable by reflected light. Most preferred are multi-zoned elements having a plurality of reagents and/or functions that are divided among the zones. Highly preferred are elements in which the zones are separate but contiguous layers, for example, a multi-layered test element as described in U.S. Pat. No. 3,992,158, issued on Nov. 16, 1976, or in U.S. Pat. No. 4,258,001, issued on Mar. 24, 1981. The test elements of said patents include an uppermost layer that functions to transport the liquid to be tested to the next adjacent layer or layers. Such uppermost layer optionally includes a reagent for the test, for example, one or more enzymes operative with the analyte of choice. The next adjacent layer or layers preferably include a matrix or binder and remaining reagents for the assay. These remaining reagents include those necessary to produce a detectable signal in increasing or decreasing amounts, e.g. a change in reflection density in response to the reaction of the analyte. More preferably, such layers are formed and mounted as an integral element, within a support frame apertured to receive a liquid drop on the uppermost layer, as described, for example, in U.S. Pat. No. 4,169,751, issued on Oct. 2, 1979.

Figure 1:
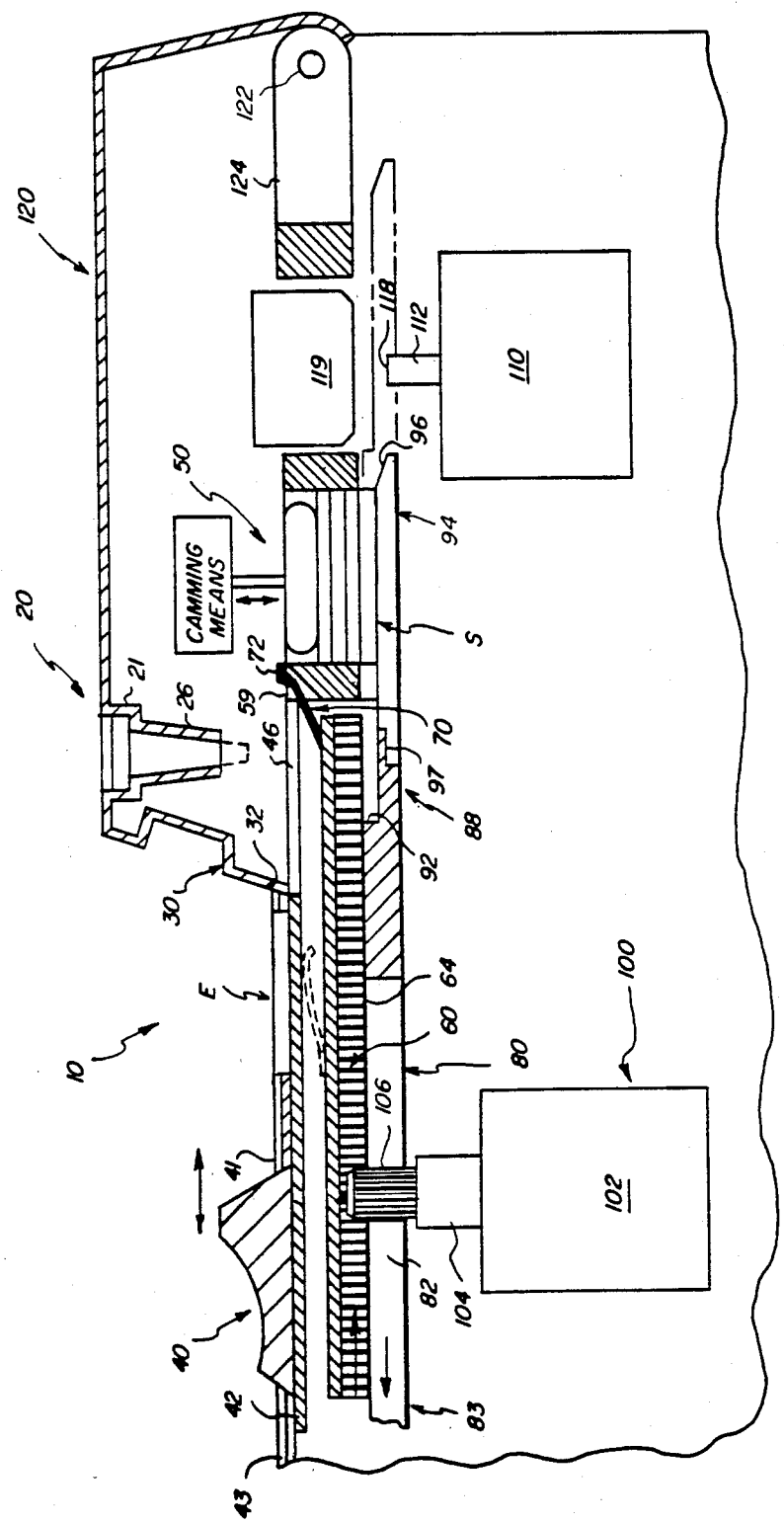
FIG. 1 is a sectional view of an analyzer and reflectometer in which the invention is useful.

A useful analyzer 10 for practicing the invention is illustrated in FIG. 1. This analyzer is described in detail in the aforesaid U.S. Ser. No. 354,859 and its corresponding European Patent Application Publication No. 88,601. The details of the aforesaid U.S. application are expressly incorporated herein by reference. More particularly, such an analyzer 10 includes a metering station 20, a storage station comprising a storage chamber or incubator 50, means 40 for moving test element E to the station 20, a detection station 110 containing a contact reflectometer, and test element moving or transport means. Metering station 20 is a molded portion of cover 120 shaped to accommodate a pipette, not shown. The moving or transport means include a member 60 for loading a test element E into chamber 50, unloading member 80 for unloading an element from the chamber, and drive means 100 for driving the loading and unloading means 60 and 80. Optionally cover 120 is pivotable, enclosing the portions that are preferably operated under controlled conditions. Cover 120 is preferably hinged at 122 to a bracket 124.

To permit a test element E to be pushed into station 20 through cover 120, the cover includes at front portion 30 thereof, a slot 32 sized to permit passage of such a test element. The test element is moved through the slot preferably by means of slide 40 that is mounted for manual reciprocation between a cover plate 41 and a support plate 42. Edge surfaces 43 of plate 41 are spaced apart to allow slide 40 to reciprocate between them.

Disposed further within cover 120, adjacent to station 20 and preferably collinear with the path traveled by slide 40 between edge surfaces 43, is the storage chamber or incubator 50, hereinafter simply "incubator". This incubator is preferably constructed in the manner described in U.S. Pat. No. 4,303,611, issued on Dec. 1, 1981, entitled "Analyzer Apparatus Featuring a Simplified Incubator," the details of which are expressly incorporated herein by reference.

To load a test element into incubator 50 from metering station 20, load means are mounted for reciprocal movement under support surface 42. Such means comprises the member 60, which is preferably centrally notched, one wall of the notch being provided with a rack gear 64. Member 60 reciprocates within a passage and further includes, at its end proximal to metering station 20, a flexible finger 70, that is spring-biased to project upwardly into the plane of the path of movement of test elements into and out of metering station 20. Slots 46 and 59 are disposed to accommodate this extension of finger 70. Tip 72 of finger 70 is curved to provide a camming surface that allows finger 70 to bend back under support surface 42 when member 60 is retracted to its most rearward, or idle, position. The flexibility of finger 70 also permits a test element to override the finger and enter metering station 20.

To unload a test element E from the bottom of the stack S on a first-in, first-out basis, a second member 80 is provided, mounted under first member 60 for reciprocal movement. Member 80 is also notched lengthwise, at 82, at least at end portion 83 thereof distal to incubator 50. A rack gear, not shown, is provided along the notch wall that is opposite to the notch wall bearing gear 64 of member 60, thereby insuring that the two members are reversely coupled to gear 106.

Such an analyzer works as follows: A test element E is pushed manually to the metering station 20. Thereafter, to move element E into incubator 50 while the camming means is raised, motor 102 drives member 60 and finger 70 to the right as shown. After an appropriate incubation time, motor 102 is reversed so that the bottom portion 88 of member 80 advances through an aperture in incubator 50. A lip 92 on bottom portion 88 picks off the bottom-most test element and carries it to a position above the read head 112 at station 110 having a contact surface 118. (Read head 112 is preferably a fiber optics head of the type described in U.S. Pat. No. 4,302,420, issued Nov. 24. 1981.) A weighted cover member 119 is raised for this step. As bottom portion 88 moves over the read station in this manner, surface 97, which contains the black and white coatings forming the black and white references of the reflectometer, passes above, and spaced from, surface 118 without contacting it. At this time, those references are scanned by the reflectometer and respective signals are generated. It is these coatings on surface 97 that may be, and preferably are, non-ideal as described above.

Alternatively, the black reference can be provided by turning off the light source at station 110 and making a reading, or by removing cover 119 and having read head 112 read an open, dark "hole." The white reference can be simply the detector detecting the light source directly. For the reflectometer of FIG. 1, this latter function could be achieved by replacing the white coating on surface 97 with a mirror, so that the incoming light of read head 112 would be reflected directly to the detection fibers in head 112.

When motor 102 reverses again to pull bottom portion 88 back to the left, a spring clip, not shown, acts to retain a test element in reading position over head 112. When bottom portion 88 is completely withdrawn to the position shown in solid in FIG. 1, such test element (not shown) is pushed by cover 119 onto the contact surface 118 for reading. Thus, the test element is read at a contact plane, corresponding to the plane of surface 118, that is spaced away from, or at a different location than, the plane of reference surface 97.

Figure 2:
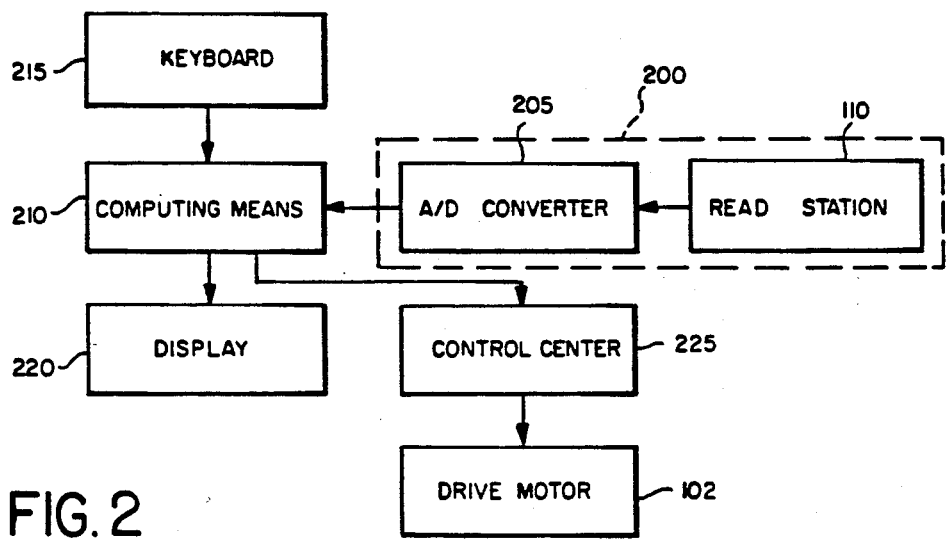
FIG. 2 is a schematic view of the control components of such an analyzer.

FIG. 2 illustrates exemplary means for controlling the analyzer. The reflectometer 200 of the analyzer comprises read station 110 containing the features described above, and an analog-to-digital converter 205. The signal emitted from the converter passes to computing means 210, which also receives input from at least a keyboard 215. Computing means 210 in turn controls a read-out means, which comprises at least a display 220 and a control center 225 that operates motor 102.

All of converter 205, computing means 210, keyboard 215, display 220 and control center 225 are conventional and require no extensive description. Means 210 preferably includes a programmable microprocessor that comprises a conventional central processing unit, for example, an Intel 8085 chip not shown, and conventional memory units comprising one or more RAM's and optionally one or more EPROM's, also not shown. Or alternatively, any other digital computer is useful.

THE METHOD

The invention concerns a method for calibrating a reflectometer of the type described above, in consideration of the difference in the detection locations of the black and white references compared to the detection location of the test elements. More specifically, a method is provided for ascertaining values of $R_{black}^{effective}$ and $R_{white}^{effective}$ for equation (1a) above.

In accordance with one embodiment of the invention, the simplest method for ascertaining $R_{black}^{effective}$ and $R_{white}^{effective}$ is to select a dark standard and a light standard that are very close in uncorrected reflectance values to the uncorrected reflectance values obtained for the black and white references, when such uncorrected reflectance values are read for the dark and light standards in the detection location used for the test elements. (Such values are read for the black and white references in their normal reference detection locations.) The selected dark and light standards are thereafter read in a reflectometer having "ideal" black and white references, known as the "referee reflectometer."

As used herein, "ideal" means a black reflectance for the black reference that is always less than the blackest sample to be tested, and a white reflectance for the white reference that is always greater than the whitest sample to be tested.

The reflectance values detected on the referee reflectometer for properly selected dark and light standards become $R_{black}^{effective}$ and $R_{white}^{effective}$, respectively, in equation (1a) above.

By "very close", what is meant is that the reflectance value read on the test reflectometer 200 for the dark standard in the test element location, is within ±0.005 of the black reference value also read on that test reflectometer but in the reference detection location. Similarly, such reflectance value read for the light standard is within ±0.05 of the value for the white references. A convenient and preferred method for making such determination is discussed hereinafter.

It can be shown by numerical simulations that the analyte concentration inferred for a sample test element by a test reflectometer is significantly more accurate if the effective reflectance used in equation (1a) is obtained from a dark standard having an uncorrected reflectance that differs from the black reference's uncorrected reflectance by no more than 0.005, and for the light standard by no more than 0.05 from the value for the white reference.

The dark and light standards comprise any material, preferably of varying shades of neutral density, such as neutrally colored polyethylene, mounted in a frame to simulate a test element. The operator selects from such standards, within the meaning of this invention, until he finds one that gives an uncorrected reflectance value, when read by the test reflectometer in the test element location using equation (2) above, that is within ±0.005 or ±0.05, respectively, of that of the black and white references read in the reference detection location.

It will be appreciated that the aforedescribed method requires no plotting of curves nor of establishing a mathematical relationship wherein A/D signals or $R_{sample}^{uncorrected}$ is a function of referee reflectances. It has the further advantage of being accurate regardless of whether such mathematical relationship is linear or not, particularly as the difference between the reflectance reading for the dark and light standards, and that of the corresponding references, approaches zero.

Figure 3:
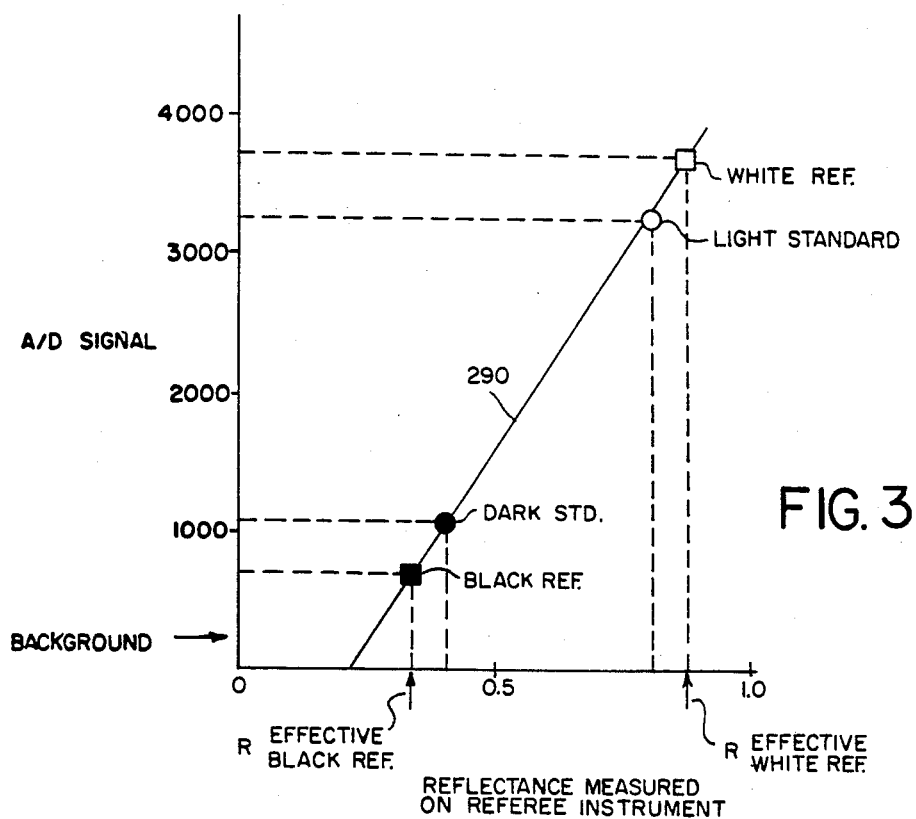
FIG. 3, illustrating one embodiment of the invention, is a plot of the digital signal obtained from the described apparatus versus reflectances measured on a referee reflectometer.

In accord with a more preferred embodiment of the invention, the dark and light standards are used to deduce the effective reflectance values of the black and white references by carrying out the method summarized in the plot of FIG. 3. (In this embodiment, the light output of the light source is made to be constant, such as by using a conventional feedback circuit, not shown, including a detector that reads the light source.) This plot is obtained by taking *any* "dark" standard, regardless of how close it is to the reflectance value of the black reference. (However, for some chemistries such as triglycerides, this is preferably within ±0.1 of the black reference's uncorrected reflectance.) The A/D signal of such dark standard is then read on the test reflectometer in the detection location of the test element. The same is done for any "light" standard, regardless of its relationship to the reflectance of the white reference, except that for some chemistries such as triglycerides, the light standard is preferably within ±0.1 of the uncorrected reflectance of the white reference. The two thus arbitrarily selected "dark" and "light" standards are also read on the referee reflectometer to obtain a reflectance for each, $R_{standard}^{referee}$. The two A/D signals measured on the test reflectometer and the corresponding referee-measured reflectances permit a linear plot to be drawn, shown as line 290, which follows the equation:

$$A/D \text{ signal} = a(\text{referee reflectance}) + b. \quad (3)$$

Thereafter, all that is necessary for the reflectometer operator to do is to read the A/D signal produced by the black reference and white reference of the test instrument, and locate these on the ordinate of the plot of FIG. 3. The corresponding abscissa values are selected from the graph line 290 (or calculated from equation (3)), and these become the calibrating terms $R_{black}^{effective}$ and $R_{white}^{effective}$, respectively, used in equation (1a) as the terms to adjust $R^{uncorr}$.

Graphical or mathematical processes, such as that of FIG. 3, whereby the reflectance of the dark standard permits determination of the effective reflectance of the black reference, are preferred to the trial and error method, in that they are more rapid and more facile.

The solid line 290 of FIG. 3 illustrates a possible example. In this case, the dark and light standards are polyethylene test elements which, when pushed through the reflectometer of FIG. 1, produce an A/D signal of about 1100 and about 3300, respectively. On a Zeiss DMC-26 reflectometer, these are assumed to produce referee reflectances of, for example, about 0.4 and about 0.8, respectively. (These values, when inserted into equation (3) allow a and b to be uniquely solved, that is, a=5500 and b=1100). When the black and white references are read on the test reflectometer of FIG. 1, in the detection location 97 shown therein, they are found to produce A/D signals of about 800 and about 3800, respectively. Using the graph of FIG. 3 or equation (3) noted above with a=5500 and b=1100, this corresponds to an $R_{black}^{effective}$ and $R_{white}^{effective}$, respectively, of about 0.3 and about 0.9.

It will be readily appreciated that the aforedescribed use of FIG. 3 is equivalent to selecting a dark standard that is within ±0.005 of the reflectance of the black reference (actually, ±0.00), and a light standard that is within ±0.05 of the reflectance of the white reference (actually ±0.00), and reading their effective reflectances on the referee reflectometer. That is, by finding the referee-reflectometer reflectance value for a given A/D reading on FIG. 3, say for the black reference, the user in effect has selected a dark standard having an uncorrected reflectance that is identical to, and therefore within ±0.005 of, the uncorrected reflectance of the black reference, and "placed" that dark standard in the referee reflectometer to determine its reflectance. The two procedures are fully equivalent.

It will be further appreciated that the analog counterpart of the A/D signal can be used, instead of the digital signal, in the graph of FIG. 3.

Once the $D_R^{ideal}$ value is calculated from equation (1a) for a test element, the corresponding analyte concentration is determined by converting the $D_R^{ideal}$ values using fluid concentration calibration values obtained from calibrator fluids, as is conventional.

Figure 4:
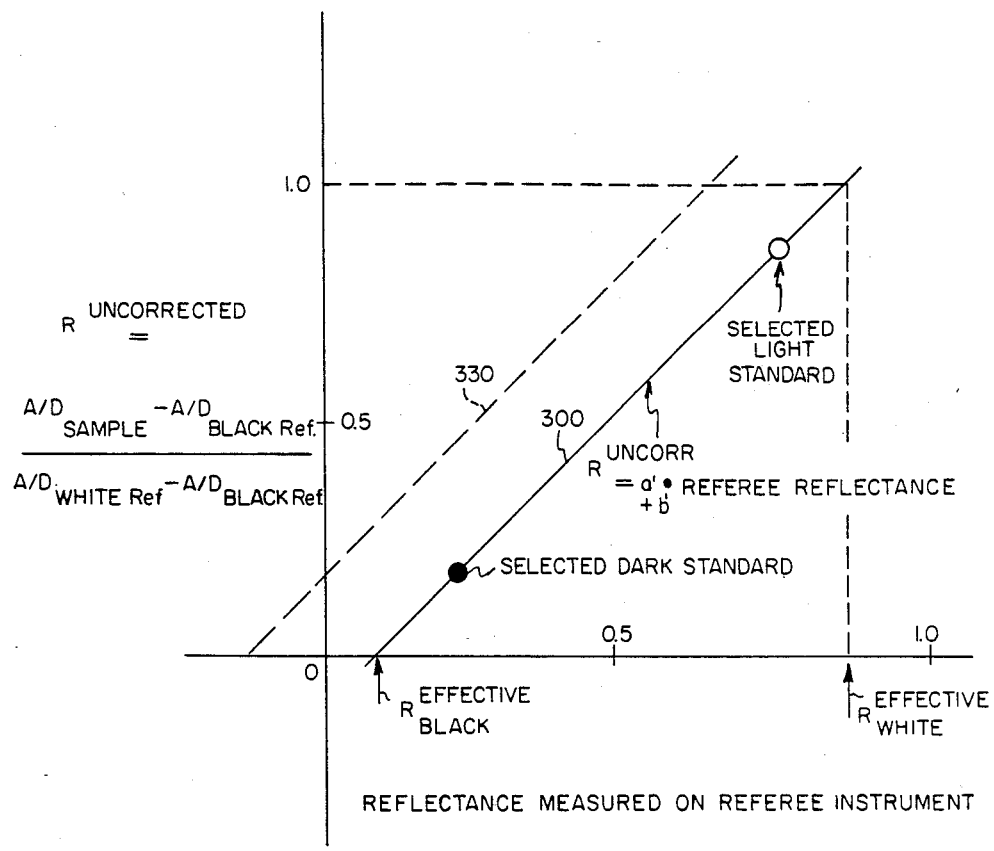
FIG. 4, illustrating other embodiments, is a plot of uncorrected reflectances obtained by the described apparatus, versus effective reflectances obtained on a referee reflectometer.

FIG. 4 is yet another way of graphically depicting the process of FIG. 3, and determining $R_{black}^{effective}$ and $R_{white}^{effective}$. In this case, the ordinate values are the result of the calculation of equation (2). That is, $R^{uncorrected}$, hereinafter $R^{uncorr}$, will equal zero *only* when the dark standard's A/D signal measured on the test reflectometer (the "sample" in the equation) equals that of the black reference; and $R^{uncorr}$ will equal 1.0 only when the light standard's A/D signal (again, the "sample") equals that of the white reference. As in the process of FIG. 3, the dark standard is selected to produce any data point, for example, an $R^{uncorr}$ of about 0.3, although preferably it is less than 0.1. Similarly, the light standard that is selected is any value, although preferably between 0.8 and 1.2, e.g. 0.9. When the standards are read for their effective reflectance on the referee reflectometer, the sloped line 300 of FIG. 4 can be drawn, or the constants of equation (4) solved:

$$R^{uncorr} = a'(\text{Referee Reflectance}) + b'. \qquad (4)$$

Then, the $R_{black}{}^{effective}$ and $R_{white}{}^{effective}$ become immediately ascertainable. That is, graphically $R_{black}{}^{effective}$ is the abscissa value where $R^{uncorrected} = 0$, and $R_{white}{}^{effective}$ is the abscissa value where $R^{uncorr} = 1$.

Such use of FIG. 4 is the same as though the user had actually selected a dark standard having an uncorrected reflectance that equalled zero (and therefore was within ±0.005 thereof), and thereafter measured such dark standard on the referee reflectometer to obtain a measured reflectance that becomes the dark standard's effective reflectance. A similar statement is true concerning the use of FIG. 4 to determine the light standard and the effective reflectance of the white reference. That is, the above-described use of FIG. 4 is equivalent to actually selecting a light standard with $R^{uncorr}$ equal to 1.0, instead of, e.g., about 0.8, and reading that light standard on the referee reflectometer to obtain the effective reflectance for the white reference.

The dashed line 330 of FIG. 4 illustrates the plot that is likely to be obtained if the black reference is simply the reflectometer with the light source turned off, or an empty cavity. The process in such a case is exactly the same, except that $R_{black}{}^{effective}$ is a negative value.

An advantage of the embodiment illustrated in FIG. 4 as compared to that of FIG. 3, is that it automatically compensates for a change in the light output of the light source or in the sensitivity of the photodetector of read head 112, from the time that the $R_{black}{}^{effective}$ and $R_{white}{}^{effective}$ are calculated, to the time of the test of the sample biological liquid. This advantage is particularly significant if the invention process of determining $R_{black}{}^{effective}$ and $R_{white}{}^{effective}$ is carried out well in advance of the sample tests, as is noted hereinafter. That is, during the latter test, it is true that, if there is a different light output or photodetector sensitivity, the A/D signal of the sample will be other than that expected for that level of analyte, when determining the curve of FIG. 4. However, $D_R{}^{ideal}$ of equation (1a) still includes the term $R^{uncorr}$, which is determined by the A/D signal of the sample as well as of the black and white references. Since the signal from the black and white references will be altered correspondingly to the alteration of the signal from the test element, due to the light source of photodetector response now operating at a different but constant level, the denominator of $R^{uncorr}$, equation (2), will be altered proportionately to the alteration in the numerator, and the relationship of FIG. 4 will be constant.

The procedure of FIG. 3 allows the references to be read in any detection location, so long as such detection location remains relatively constant during subsequent actuations of the instrument. In other words, all readings, especially those from the references, are transformed to the corresponding reflectances anticipated to be measured in the test element detection location, regardless of where the references are actually observed.

An understanding of the invention can be further aided by the following explanation:

Once the dark standard's A/D value or uncorrected reflectance value from the test reflectometer is plotted relative to its corresponding referee reflectance value, ascertained by the referee reflectometer, and the same is done for the light standard, a relationship is established for A/D value (or uncorrected reflectance value, FIG. 4) obtained on the test reflectometer for any element read in the test element detection location. Now if that same element should be detected in a location farther away from the detector than the test element detection location, the effect will be to give a different A/D value, or a different uncorrected reflectance value. By means of the aforementioned relationship, the different value has a unique corresponding effective reflectance as determined by the referee reflectometer. That corresponding reflectanced does not "care" whether the A/D value (or uncorrected reflectance value, FIG. 4) is different because the intrinsic reflectance value is different (as in the case with the black reference, compared to the dark standard), *or* because the detection location differs (as is also the case of the black reference), or *both*.

Although the mathematical relationship described in each of FIGS. 3 and 4 is a linear one, non-linear relationships are also useful, for example, a quadratic. The selection of the mathematical relationship depends upon the nature of the optics of the reflectometer. The reflectometer of FIG. 1 exhibits essentially, signal that is linearly dependent upon reflectivity, and for this reason a linear relationship is preferred. That is, each and every one of the points on the curves of FIGS. 3 and 4 represents, within reasonable experimental error, what one would have measured as the referee reflectance on the referee reflectometer if standards were checked for each A/D point represented by the curve of FIG. 3, or each $R^{uncorr}$ point represented by curve 300 of FIG. 4.

MOST PREFERRED EMBODIMENT

The process described above is preferably carried out first at the factory, as a primary calibration step. That is, once $R_{black}{}^{effective}$ and $R_{white}{}^{effective}$ have been calculated, they are recorded or stored in memory in computing means 210. Thereafter, when the test reflectometer is used to read test elements using the displaced black and white references, equation (1a) is used to obtain $D_R{}^{ideal}$ using the previously recorded values for $R_{white}{}^{effective}$ and $R_{black}{}^{effective}$.

Figure 5:
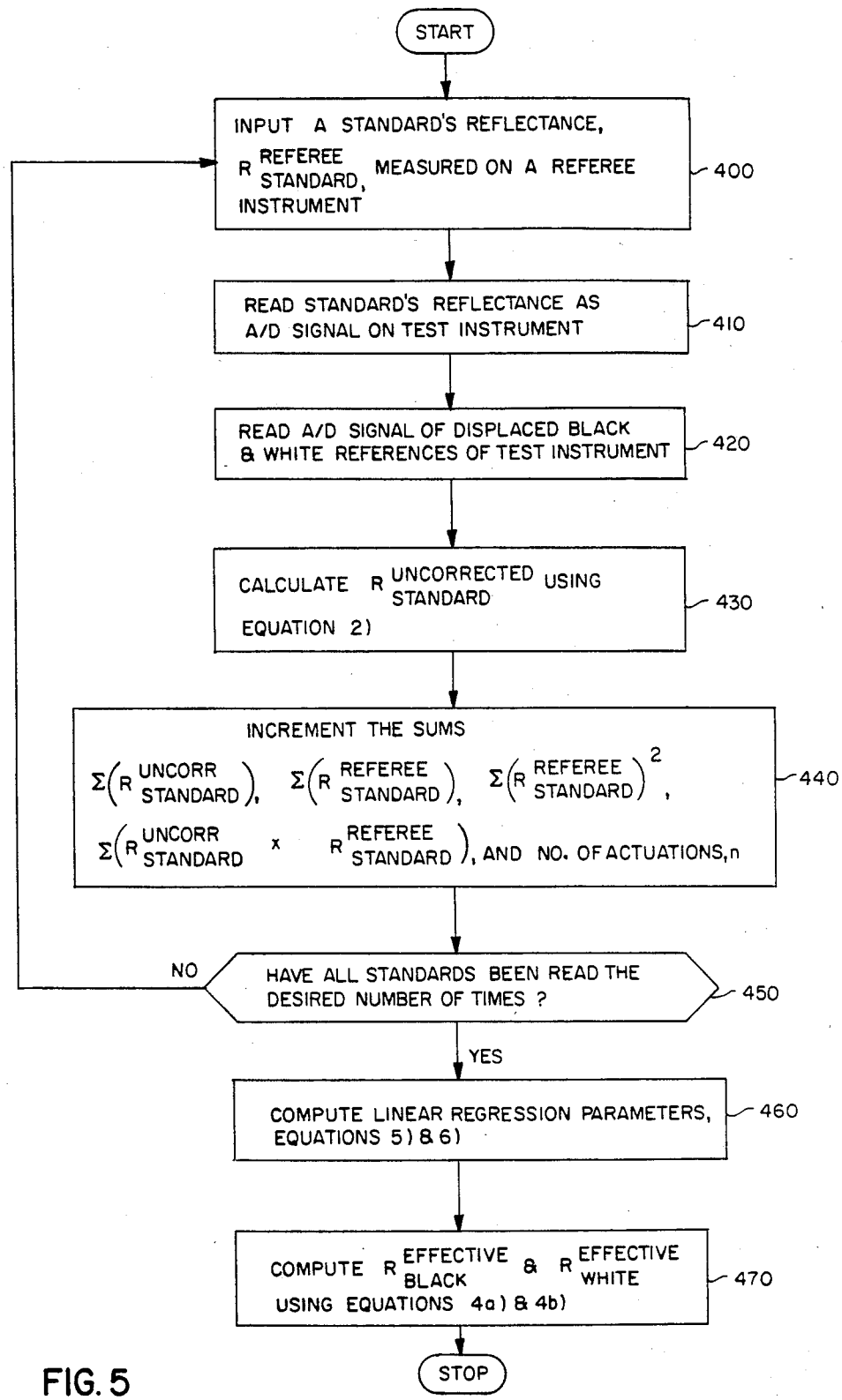
FIG. 5 is a flow chart for programming the computing means of the described apparatus to carry out the invention.

FIG. 5 is a logic flow chart useful in programming a microprocessor of means 210 to carry out the aforedescribed method. From this flow chart, a program routine is readily determinable using conventional programming techniques. Specifically, a first standard, either dark or light, is measured on a referee reflectometer to determine a first reflectance ($R_{standard}{}^{referee}$) (using the nomenclature of FIGS. 3 and 4). That value of $R_{standard}{}^{referee}$ is entered into the algorithm, box 400. The reflectance of this standard is then read, box 410, in the plane of the test elements in the test analyzer of choice, such as that of FIG. 1. Before or after that reading, the black and white references are read but while in their own displaced location, box 420. (That is, box 420 can be before box 410, rather than after it.) Next, box 430, computing means 210 calculates $R_{standard}{}^{uncorrected}$, equation (2), where the standard represents the "sample" in the equation. Thereafter the process increments, box 440, the sums of the new $R_{standard}{}^{uncorrected}$ along with the sums of the terms $R_{standard}^{referee}$, $(R_{standard}^{referee})^2$, $(R_{standard}^{uncorr} \cdot R_{standard}^{referee})$ and the number of actuations. Finally, the condition is ascertained, box 450, as to whether all the standards (2, if just dark and light are used) have been read the desired number of times. If so, then computing means 210 computes the linear regression parameters, box 460, using the conventional values of $$\text{slope} = \{n\Sigma(R_{standard}^{referee} \cdot R_{standard}^{uncorr}) - \quad (5)$$
$$\Sigma(R_{standard}^{referee}) \cdot \Sigma(R_{standard}^{uncorr})\}/$$
$$\{n\Sigma(R_{standard}^{referee})^2 - [\Sigma(R_{standard}^{referee})]^2\},$$

and $$\text{intercept} = \{\Sigma(R_{standard}^{referee})^2 \cdot \Sigma(R_{standard}^{uncorr}) - \quad (6)$$
$$\Sigma(R_{standard}^{referee} \cdot R_{standard}^{uncorr}) \cdot \Sigma(R_{standard}^{referee})\}/$$
$$\{n\Sigma(R_{standard}^{referee})^2 - [\Sigma(R_{standard}^{referee})]^2\}.$$

Thereafter, box 470, means 210 computes $R_{black}^{effective}$ and $R_{white}^{effective}$ using the corresponding values for $R^{uncorr}=0$ and $R^{uncorr}=1$ (in equation 4), namely $$R_{black}^{effective} = -\text{intercept/slope, and} \quad (4a)$$

$$R_{white}^{effective} = (1-\text{intercept})/\text{slope}. \quad (4b)$$

It is these finally determined values that are recorded or stored for use in equation (1a) by computing means 210, to calculate corrected densities of the samples.

EXAMPLE

To further illustrate, consider a reflectometer comprising a light source which simultaneously illuminates a test-element position and black and white references. Suppose further that the black and white references are located twice as far as is the test element from the lamp, and the reflectometer includes a photodetector which can quantitate the light reflected from either the test-element position or the twice-distant references. The dimensions of the lamp, detector, test elements, and references are all small compared to the distances separating the noted reflectometer parts so that the light intensity from one part seen at the vantage point of the subsequent part obeys the well-known $1/r^2$ dependence, where "r" is the distance.

Comparison of the signals obtained with a white reference having reasonable reflectivity (95% intrinsic reflectance), a black reference of 5% intrinsic reflectance and a test element also of 95% intrinsic reflectance so as to be identical to the white reference, demonstrates the superiority of the use of "effective reflectance" versus "intrinsic reflectance" for references observed at locations other than the test element detection location. Both the test element and the white reference produce 95% reflectance readings on the referee reflectometer. But the extra distance between light source and references in the instrument under consideration means that the light intensity from the lamp at either reference is only one quarter of the intensity at the test element. In addition, the doubled distance from reference to detector implies that the overall light flux reaching the detector via the white reference is only one-sixteenth of the intensity seen from the test element. Similarly, the intensity from the black reference would be one-sixteenth of the intensity seen if the black reference were located at the position of the test element. Knowing the intensity, the $R_{white}^{effective}$ becomes 1/16 of the 95% value, and $R_{black}^{effective}$ becomes 1/16 of the 5% value, or 5.94% and 0.31%, respectively. These are, in fact, the values that would occur if such a test were actually run using the aforedescribed method of FIG. 4. Thus, $R^{uncorr}$ for the 95% reflective test element would be, equation (2):

$$R_{sample}^{uncorr} = \frac{A/D_{test\ element} - \frac{1}{16} \times \frac{5\%}{95\%} A/D_{test\ element}}{\frac{1}{16} A/D_{test\ element} - \frac{1}{16} \times \frac{5\%}{95\%} A/D_{test\ element}}$$

Or, $R_{sample}^{uncorr} = A/D_{test\ element} \left(1 - \frac{1 \times 5}{16 \times 95}\right) /$ $A/D_{test\ element} [(1/16) - (1/16) \times 5/95]$.

Since $A/D_{test\ element}$ drops out, $$R_{sample}^{uncorr} = 1683\%. \quad (7)$$

Since from equation (1a), $R_{sample}^{corrected} = R_{sample}^{uncorrected} \cdot (R_{white}^{effective} - R_{black}^{effective}) + R_{black}^{effective}$, one should be able to use the value calculated in (7) above. Although the references exhibit a relatively small amount of intrinsic non-ideality, attempts to ascertain $R_{sample}^{corrected}$ using the references' intrinsic reflectances are inadequate to rectify the effects of diminished intensity from the references due to their non-coincidence with the test element detection location. That is, $(R_{sample}^{corrected})$intrinsic$=(1683\%)(95\% - 5\%)+(5\%)+1520\%$ whereas the answer should be 95%, as given in the hypothetical. But if the *effective* reflectances for the references as determined by this invention are used (in this case 5.94% and 0.31% for $R_{white}^{effective}$ and $R_{black}^{effective}$, respectively), the desired corrected reflectance for the test element is produced:

$(R_{sample}^{corrected})$effective$=(1683\%)(5.94\%-0.31\%)+0.31\%=95\%$.

This example indicates that use of an effective reflectance value as per the invention improves the instrument's results.

The invention has been described in detail with particular reference to preferred embodiments thereof, but it will be understood that variations and modifications can be effected within the spirit and scope of the invention.

What is claimed is:

1. A method of calibrating a reflectometer containing a black reference and a white reference that are detected in a first location that is placed at a distance from the light source of the reflectometer that is optically different from the distance of the location of test elements from said light source when positioned for detection, said method featuring calibration factors representing the effective reflectances for each of said references which compensate for said optically different distances of such test elements and said black and white references, said method comprising the steps of
(a) selecting a dark standard and a light standard;
(b) ascertaining, on a second reflectometer, the reflectance of the dark standard and the light standard;

(c) measuring an analog or digital signal for both of said standards at a distance from said light source that is optically the same as said test element distance location using said first reflectometer;

(d) calculating a linear relationship between the reflectances of step (b) and the signals of step (c);

(e) measuring on said first reflectometer an analog or digital signal for both of said references while in said first location;

(f) ascertaining the corresponding effective reflectances from said linear relationship, using said signals measured in step (e); and (g) calibrating said reflectometer using said effective reflectances as said calibration factors.

2. A method of calibrating a first reflectometer containing a black reference and a white reference that are detected in a first location that is placed at a distance from the light source of the reflectometer that is optically different from the distance of the location of test elements from said light source when positioned for detection, said method featuring calibration factors representing the effective reflectances for each of said references which compensate for said optically different locations of such test elements and said black and white references, said method comprising the steps of (a) selecting a dark standard and a light standard of any value, (b) ascertaining, on a second reflectometer, the reflectance of the dark standard and the light standard;

(c) determining an uncorrected reflectance for each of said standards at a distance from said light source that is optically the same as said test element distance, using said first reflectometer and the equation $$R_{standard}^{uncorrected} = (S_{standard} - S_{black\ ref})/(S_{white\ ref} - S_{black\ ref})$$

wherein $S_{standard}$ is an analog or digital signal generated on said first reflectometer using each of said dark and light standards, $S_{black\ ref}$ is such analog or digital signal of said black reference of said first reflectometer, and $S_{white\ ref}$ is such analog or digital signal of said first reflectometer white reference;

(d) calculating a linear relationship between the reflectances of step (b) and the uncorrected reflectances of step (c);

(e) selecting as said effective reflectances of said black and white references, the value of the respective reflectances such dark and light standards, would give on said second reflectometer if their reflectances determined in said step (c) were zero and 1.0, respectively, using the relationship calculated in said step (d); and (f) calibrating said first reflectometer using said effective reflectances as said calibration factors.

3. A method as defined in claim 1 or 2, and further including the step of correcting uncorrected reflectance readings obtained for test elements containing liquid analyte, using said effective reflectances for said black and white references previously recorded.

* * * * *